United States Patent [19]

Burkholder

[11] 3,978,142

[45] Aug. 31, 1976

[54] PROCESS FOR PRODUCING POLYPHENOLS

[75] Inventor: Ward J. Burkholder, Baton Rouge, La.

[73] Assignee: The Goodyear Tire & Rubber Company, Akron, Ohio

[22] Filed: Jan. 14, 1974

[21] Appl. No.: 433,393

[52] U.S. Cl. .................... 260/621 C; 260/610 A; 260/610 B; 260/622 R; 260/625; 260/623 R
[51] Int. Cl.² .......................................... C07C 37/08
[58] Field of Search ........ 260/610 A, 610 B, 621 C, 260/625, 622 R, 623 R

[56] References Cited
UNITED STATES PATENTS

| | | | |
|---|---|---|---|
| 2,856,433 | 10/1958 | Thompson | 260/610 A |
| 3,190,924 | 6/1965 | Sodomann et al. | 260/610 B |
| 3,798,277 | 3/1974 | Sugiyama et al. | 260/621 C |

*Primary Examiner*—Norman Morgenstern
*Attorney, Agent, or Firm*—Browning & Bushman

[57] ABSTRACT

A portion of a recycle stream obtained from the reaction mixture resulting from the oxidation of an aryl tertiary alkane and containing primarily aralkyl tertiary monohydroperoxide, unreacted aryl tertiary alkane, a minor amount of aralkyl tertiary polyhydroperoxide and other by-products is separated to obtain a fraction containing substantially all of the polyhydroperoxide and at least some of the by-products, the fraction then being introduced into a rearrangement zone to convert at least a portion of the polyhydroperoxide to the corresponding polyphenol.

17 Claims, 1 Drawing Figure

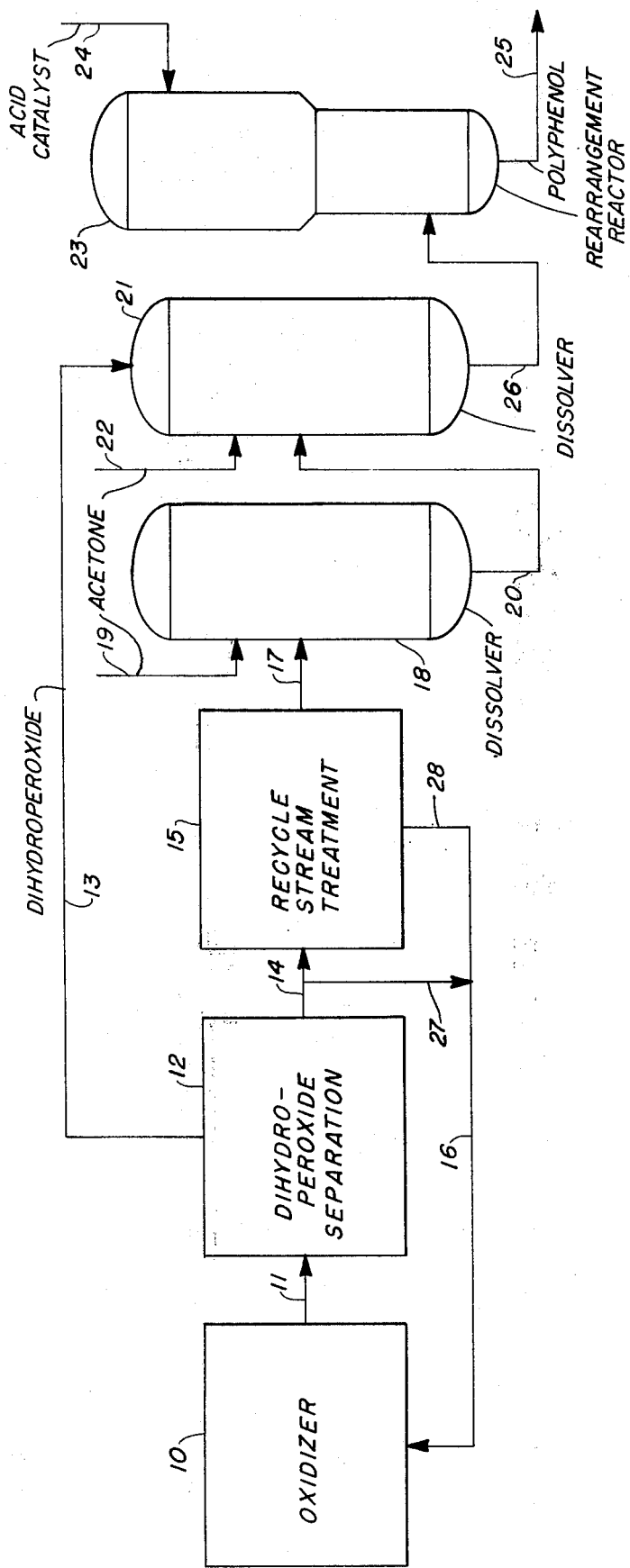

PROCESS FOR PRODUCING POLYPHENOLS

BACKGROUND OF THE INVENTION

The present invention relates to the production of polyphenols and, more specifically, to the production of polyphenols from aralkyl tertiary hydroperoxides.

In the production of aralkyl tertiary polyhydroperoxides such as for example p-diisopropylbenzene dihydroperoxide, there is also produced the corresponding monohydroperoxide. Indeed, the rate of formation of the monohydroperoxide is approximately proportional to the concentration of the aryl tertiary alkane in the reaction mixture and that of the dihydroperoxide to the concentration of the monohydroperoxide. The reaction, however, comes to a virtual standstill before all of the monohydroperoxide is converted to the dihydroperoxide and consequently for a given amount of the aryl tertiary alkane only a small proportion of the dihydroperoxide is obtained.

It is known that the oxidation reaction can be conducted so as to yield a considerably higher amount of the aralkyl tertiary dihydroperoxide if the dihydroperoxide is separated from the oxidation reaction mixture alternately or concurrently with the oxidation reaction while the oxidation is continued with the remaining reaction mixture. As a practical matter, in a continuous reaction, the dihydroperoxide is continuously removed from the reaction mixture and the remaining portion of the oxidation reaction product is recycled to the oxidation reaction to convert the large amounts of monohydroperoxide present in the recycle stream to dihydroperoxide.

Unfortunately, the oxidation reaction product from which the dihydroperoxide has been removed and which is recycled to the oxidation reaction, in addition to containing large amounts of the monohydroperoxide, also contains undesirable by-products and impurities which are quite detrimental to the efficiency of the oxidation reaction. For example, it is known that in such reactions keto aryl tertiary alkanols, aralkyl tertiary dialkanols and other by-products are also produced. These materials, particularly the keto aryl tertiary alkanols hinder the oxidation reaction. As a consequence of the above-described recycle of the substantially dihydroperoxide free oxidation reaction product to the oxidation reactor, these impurities and by-products continue to build up to the point where, it the oxidation reaction is to be conducted efficiently and economically, it may become necessary to completely discharge the reactor contents and charge the reactor with fresh reactants.

In co-pending application, Ser. No. 285,481, now abandoned, is described a process wherein the by-products, discussed above, which would normally build up in the reactor are purged from the system, preferably in a continuous manner, thereby maintaining the reactor in a substantially steady-state condition. Briefly the process involves taking a portion of the oxidation reaction product stream after removal of the greater part of the polyhydroperoxide and separating the substantially polyhydroperoxide free reaction product into at least two fractions, one of which contains most of the impurities and by-products which have a deliterious effect on the oxidation reaction. While the process described in the aforementioned co-pending application works remarkably well at maintaining the desired oxidation rate, certain problems are presented. For one, the fraction which contains the undesirable by-products and impurities also contains a significant amount of the monohydroperoxide. Such a condition poses a disposal problem which is, at best, economically undesirable and, at worst, dangerous, the monohydroperoxide being quite reactive and under certain conditions explosive. Moreover, the fraction containing the by-products also contains a small but economically significant amount of the polyhydroperoxide which, if recoverably, could be converted into the desired end product, the polyphenol. However, separation and recovery of the polyhydroperoxide from the by-product laden fraction is not economical.

SUMMARY OF THE INVENTION

It is therefore an object of the present invention to provide an improved process for the production of polyphenols from aralkyl tertiary polyhydroperoxides.

A further object of the present invention is to provide a process for treating an oxidation reaction product obtained by the oxidation of an aryl tertiary alkane with an oxygen-containing gas to produce a polyphenol.

An important object of the present invention is to provide a process for the production of polyphenols wherein aryl tertiary polyhydroperoxides are converted to such polyphenols in the presence of oxidation reaction by-products.

These and other objects of the present invention will become apparent from the drawing, the description given herein and the appended claims.

Basically, the process of the present invention involves a novel method of treating a portion of an oxidation reaction product obtained by oxidizing an aryl tertiary alkane with an oxygen-containing gas at elevated temperatures in such a fashion that polyhydroperoxide can be rearranged to the corresponding polyphenol in the presence of by-products obtained in the oxidation reaction. According to the process, a portion of the oxidation reaction product which has been freed of the greater part of the polyhydroperoxide produced in the oxidation reaction, is separated into a first or light fraction containing primarily unreacted aralkyl tertiary alkane and monohydroperoxide and a second or heavy fraction containing a minor amount of polyhydroperoxide in addition to monohydroperoxide and oxidation reaction by-products, is introduced into a rearrangement zone wherein the polyhydroperoxide is converted to the desired corresponding polyphenol without prior removal of the oxidation reaction by-products, the monohydroperoxide being converted to an easily disposable phenol.

BRIEF DESCRIPTION OF THE DRAWINGS

The single FIGURE is a diagrammatic representation of the process of the present invention.

DESCRIPTION OF THE PREFERRED EMBODIMENT

The process to which the present invention is directed involves the production of aralkyl tertiary hydroperoxides which are obtained by the oxidation of an alkyl aromatic hydrocarbon and more specifically an aryl tertiary alkane which may contain other substituents and the conversion of the polyhydroperoxides to the corresponding polyphenols. The term aryl tertiary alkane as used herein and from which the hydroperoxides are obtained is intended to include compounds defined by the formulas:

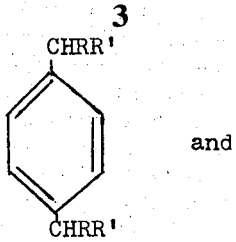

and

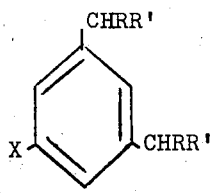

wherein R and R' may be the same or different and are alkyl or cycloalkyl and X is one of the group, hydrogen, lower alkyl, —CHRR', halogen and —NO$_2$. The alkyl radical may be straight chain or branched chain but perferably is straight chain having 1–2 carbon atoms. Non-limiting examples of such compounds include m- and p-diisopropylbenzene, m- and p-di-sec-butylbenzene, isopropyl-4-sec-butylbenzene, isopropylbenzene-3-sec-butylbenzene, 1, 3, 5-triisopropylbenzene, 3, 5-diisopropyltoluene, 3, 5-di-isopropylchlorobenzene and 3, 5-diisopropylnitrobenzene and the like. The oxidation of the above described aryl tertiary alkanes results in the formation of aralkyl tertiary hydroperoxides having the formulas

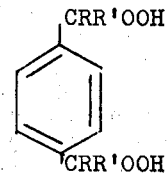

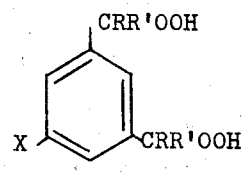

wherein R and R' have the same significance as in the previously described formulas for the aryl tertiary alkanes but wherin X can also be —CRR'OOH as well as the above named groupings. Non-limiting examples of such aralkyl tertiary hydroperoxides include m- and p-a, a, a', a'-tetramethyl-xylylene dihydroperoxide, m- and p-a, methyl, a ethyl, a' methyl, a'-ethyl xylylene dihydroperoxide, 1, 3, 5-triisopropylbenzene dihydroperoxide, 3, 5-diisopropyltoluene dihydroperoxide, 3, 5-diisopropylchlorobenzene dihydroperoxide, 3, 5-diisopropylnitrobenzene dihydroperoxide and the like, the designation $a$ referring to the Greek letter alpha.

The oxidation reaction is generally carried out in the liquid phase in the presence of an oxygen containing gas which of course may be pure oxygen or a gaseous mixture containing oxygen, such as air, and may with advantage include suitable proportions of ozone. It is generally preferred in the oxidation reaction to adjust the reaction parameters and the quantity of oxygen containing gas in such a way that an excess of oxygen over that absorbed by the reaction mixture is introduced therein. Such an excess may vary over wide limits but it has generally been found that an excess of at least 10% is preferred.

While not absolutely necessary, it is preferable to perform the oxidation reaction in the presence of alkali substances such as oxides or hydroxides of the alkali and/or alkaline earth metals, or their salts of weak inorganic or organic acids such as the carbonates, bicarbonates and the acetates or in the presence of other basic substances such as ammonia. The presence of the basic materials in the oxidation reaction retards the development of excessive acidity due to the formation of carboxylic acids which in turn hinder the oxidation reaction.

The oxidation reaction may be conducted over a wide range of temperatures as for example from 50°–150°C. When the reaction is conducted in the homogeneous phase suitable temperatures will range from between 70°–120°C and more preferably between 80° and 110°C at ambient pressures. Under heterogeneous conditions, as for example in the presence of water, temperatures between 85° and 100°C and preferably around 90°C have been found to be suitable at ambient pressure. The oxidation reaction may be conducted sub-atmospheric, atmospheric sub-atmospheric or super-atmospheric pressure, the latter with consequent broadening of the temperature range. Catalysts may be employed in the reaction if desired.

As noted, when an oxidation reaction of the type under consideration is continued for a protracted time such as occurs in a continuous process, the rate of production of the dihydroperoxide on the basis of a constant reaction volume decreases progressively. This is due to the build up in the oxidation reaction product of undesirable by-products such as keto aryl tertiary alkanols, as for example m- or p-acetyl-2-hydroxy isopropylbenzene alkanols, aralkyl tertiary dialkanols and other, usually heavier, higher boiling materials. The resulting fall in rate of the oxidation reaction, although slow, ultimately makes it necessary to stop the oxidation and to remove, in one way or another, the interfering products. Complete cessation of the reaction is economically undesirable and consequently is to be avoided if at all possible.

In the typical process for the production of dihydroperoxides, the oxidation reaction product is treated to remove most and, if possible, all of the polyhydroperoxide. This can be accomplished by techniques well known in the art. For example, processes for separating dihydroperoxides from the oxidation reaction mixture are disclosed in U.S. Pat. Nos. 2,856,432, 3,190,924, 2,856,433 and 3,190,923.

The portion of the oxidation reaction mixture remaining after the polyhydroperoxide has been removed is rich in the corresponding monohydroperoxide and contains lesser amounts of the impurities noted above, i.e. the keto aryl tertiary alkanols, the aralkyl tertiary dialkanols and the like plus a minor but economically significant amount of the polyhydroperoxide. According to the process set forth in co-pending application Ser. No. 285,481, pertinent parts of which are herein incorporated by reference, at least a portion of the oxidation reaction mixture, substantially free of the polyhydroperoxide is treated in a separation zone to obtain a first or light fraction which contains primarily monohydroperoxide and unreacted aryl tertiary alkane and a second or heavy fraction containing the aforementioned by-products, the monohydroperoxide and a minor amount of the polyhydroperoxide. As noted, this heavy fraction not only presents a direct disposal problem and hence an indirect economic burden because of the large amount of monohydroperoxide present, but likewise presents a direct economic problem because of the fact that it represents a loss of the polyhydroperoxide, the precursor of the desired polyphenol. According to the process of the present invention this heavy fraction is treated in such a fashion that the polyphenol is obtained from the polyhydroperoxide and the monohydroperoxide is converted to a more easily disposable phenol the process requiring no prior separation of the by-products.

To more fully explain the invention, reference is made to the accompanying figure. While the process, as noted above, is applicable to the production of numerous aralkyl tertiary polyhydroperoxides produced from a wide variety of aryl tertiary alkanes, the invention will be described with particular reference to the production of p-diisopropylbenzene dihydroperoxide produced from the liquid phase oxidation of p-diisopropylbenzene in the presence of a dilute aqueous caustic solution.

Referring then to the drawing, an oxidation reaction product, obtained as described above and containing unreacted p-diisopropylbenzene, p-diisopropylbenzene dihydroperoxide, p-diisopropylbenzene monohydroperoxide and by-products such as p-acetyl-a-hydroxyisopropylbenzene, p-a, a'-dihydroxydiisopropylbenzene along with other by-products, is removed from reactor 10 through line 11 and transferred to dihydroperoxide separation zone 12. As noted, separation of the bulk of the dihydroperoxide present in the oxidizer reactor effluent may be accomplished by numerous methods. The bulk of the dihydroperoxide produced in oxidizer 10 plus other materials used in the separation zone is removed via line 13 for further processing, discussed more fully hereafter. The oxidation reaction mixture, free of the greater portion of the dihydroperoxide, passes out of dihydroperoxide separation zone 12 via line 14, a portion entering recycle stream treatment zone 15, a second portion being recycled to oxidizer 10 via lines 27 and 16.

In recycle stream treatment zone 15, the portion of the substantially dihydroperoxide free oxidation reaction effluent from line 14 is separated, as per the process set forth in co-pending application Ser. No. 285,481, into a lighter fraction containing primarily monohydroperoxide and unreacted p-diisopropylbenzene which is then recycled via lines 28 and 16 to oxidizer 10. A second, heavier fraction obtained in recycle stream treatment zone 15 and which contains a large amount of monohydroperoxide, most of the aforementioned by-products and substantially all of the dihydroperoxide entering treatment zone 15 via line 14 is passed via line 17 into a dissolver 18 where it is mixed with a suitable solvent such as acetone entering via line 19. The substantially homogeneous mixture of acetone and the second fraction from the treatment zone 15 passes via line 20 into a second dissolver 21 into which is also introduced, through line 13, the dihydroperoxide rich fraction recovered from separation zone 12 plus additional acetone or other such suitable solvent through line 22.

The effluent from dissolver 21 containing a mixture or solution of the solvent (acetone), the dihydroperoxide rich fraction from separation zone 12 and the second, or heavier fraction from treatment zone 15 passes via line 26 into a rearrangement reactor 23 where the hydroperoxides are cleaved, generally employing an acid catalyst, entering via line 24, to produce a ketone and the corresponding phenol, if a monohydroperoxide is present, or a polyphenol, if a polyhydroperoxide is present. The effluent from reactor 23 containing the acid catalyst, the cleavage products of the hydroperoxides, any of the above mentioned unreacted by-products and any other products are removed from reactor 23 through line 25 for recovery of the polyphenol, i.e. the hydroquinone.

As noted, the second or heavier fraction from recycle treatment zone 15 contains unwanted by-products in addition to relatively large amounts of the monohydroperoxide and relatively smaller amounts of the dihydroperoxide. In general, the polyhydroperoxide content of the heavy or second fraction will range from about 5 to about 25% by weight, the monohydroperoxide content ranging from about 40 to about 65% by weight. It is to be noted that the second or heavy fraction contains substantially all, i.e. greater than 90% by weight of the polyhydroperoxide originally present in the stream going to zone 15. The heavier fraction from recycle treatment zone 15, which in reality can be considered a purge stream from the oxidizer reaction product mixture, will contain generally from about 5 to about 35% by weight or by-products. While other by-products will be present, the most commonly found by-products include a-hydroxy-a'-hydroperoxydiisopropylbenzene, p-acetyl-a-hydroxyisopropylbanzene and p-a, a'-dihydroxydiisopropylbenzene. While the by-products will comprise some hydroperoxy compounds, the term by-products is not intended to include the aralkyl tertiary monohydroperoxide which, of course, is a precursor to the polyhydroperoxide. Employing the process of the present invention, the dihydroperoxide present is converted directly to the diphenol, i.e. hydroquinone, without the necessity for expensive processing to effect prior removal of the by-products. Also, the monohydroperoxide is converted to the monophenol, i.e. p-isopropylphenol, which can then be relatively easily disposed of. It will be recognized that the disposal of a hydroperoxide presents much more difficulty than the disposal of a relatively inert phenolic material. Thus, an important economic advantage is realized by the process in that the product yield of the desired polyphenol is effectively increased. At the same time, the process significantly minimizes a particularly dangerous disposal problem in that the monohydroperoxide is converted to a less reactive species. These results are accomplished basically with no further processing other than the dissolution of the heavy fraction from recycle stream treatment zone 15 in a suitable solvent such as acetone.

It is not necessary that the heavier or second fraction from treatment zone 15 be combined with the dihydroperoxide rich fraction removed from the dihydroperoxide separation zone 12 prior to introduction into the rearranger. Indeed, the effluent from dissolver 18 could be fed to a separate rearranger if desired. However, combination of the two streams in dissolver 21 and common feeding to the rearranger reduces the amount of equipment needed and, accordingly, contributes to the overall economic advantage of the process. When the two streams are combined, the weight ratio of the polyhydroperoxide rich fraction from separation zone 12 to the second or heavier fraction from zone 15, will be from about 5:1 to about 20:1 without regard to acetone or other such solvent employed to dissolve the respective streams in dissolvers 18 or 21. In general, the polyhydroperoxide, e.g. dihydroperoxide, content of the stream from separation zone 12 will range from about 20 to about 40% by weight. However, the stream from zone 12 may contain much larger amounts of the dihydroperoxide depending on the separation technique employed. Obviously, other components will also be present.

As noted, a solvent such as a ketone is employed both in dissolvers 18 and 21 to dissolve the streams from zones 15 and 12, respectively. Preferably the solvent employed to dissolve either the stream from zone 12, i.e. the stream containing the greater portion of the dihydroperoxide separated from the oxidation reaction product, or the stream from recycle treatment zone 15 will be the same as the ketone obtained from cleavage or rearrangement of the polyhydroperoxide. For example, in the case where the polyhydroperoxide is paradiisopropylbenzene dihydroperoxide, the cleavage ketone comprises acetone. Accordingly, acetone is conveniently used in the dissolvers as it minimizes further separation problems. Other ketones and indeed other solvents may be employed if desired.

In the rearrangement zones, cleavage of the hydroperoxides is most conveniently carried out by acid catalysis employing strong mineral acids such as sulfuric acid, phosphoric acid, hydrochloric acid, or Lewis acids such as borontrifluoride, aluminum chloride, etc. The acid catalyzed rearrangement of the hydroperoxides is well known and processes, including operating conditions, are abundantly set forth in the prior art and well known by those skilled in the art. Generally speaking, any commonly employed cleavage catalyst can be employed in the rearrangement zone, examples of which are set forth in references such as U.S. Pat. Nos. 3,376,352, 2,718,172, 2,626,281 and 3,187,052. Preferably, the rearrangement is carried out in the presence of a mineral acid and, more especially, in the presence of sulfuric acid. The precise amount of acid employed in the rearrangement zone will, of course, depend upon the amount of hydroperoxide fed thereto, care being taken to avoid the addition of excessive amounts of acid which could cause side reactions or degradation of the desired product. However, sufficient acid is added to ensure that all hydroperoxides fed to the rearrangement zone will be cleaved to the corresponding phenol or polyphenol and the resulting ketone.

The reactor employed in the rearrangement zone can comprise a stirred reactor, a tubular reactor or any other reactor usually employed for such processes. Stirred reactors or backmix reactors for carrying out the cleavage or rearrangement reaction are well known and described in such references as U.S. Pat. Nos. 3,376,352, 2,663,735, 3,187,052, and 3,626,281. It will be apparent that the operating parameters in the rearranger will depend upon the composition of the feed, the type of reactor employed, etc.

Once the hydroperoxides have been rearranged or cleaved to the corresponding phenol or polyphenol and ketone, the rearrangement reaction product must be neutralized to eliminate the excess acid usually employed, and the polyphenols must then be separated for purification. This can be carried out by methods well known and described in the prior art.

To further illustrate the process, the following non-limiting example is presented. Unless otherwise indicated, all proportions are by weight.

EXAMPLE

A process system basically as shown in the accompanying diagram was employed. The rearranger reactor was a stirred reactor operated under the following conditions:

| Temperature | 170–180°F |
|---|---|
| Pressure | 18–20 psi |

The streams for processing were obtained from the liquid phase oxidation of paradiisopropylbenzene. The heavy fraction from recycle stream treatment zone 15 had the following approximate composition:

| Stream A | % |
|---|---|
| p-diisopropylbenzene dihydroperoxide | 14.7 |
| p-diisopropylbenzene monohydroperoxide | 52.1 |
| a-hydroxy-a'-hydroperoxydiisopropylbenzene | 4.9 |
| p-diisopropylbenzene | 0.9 |
| Water | 1.0 |
| p-acetyl-a-hydroxyisopropylbenzene | 7.3 |
| Others | 19.1 |

The feed to dissolver 21, i.e. the stream from dihydroperoxide separation zone 12, had the following approximate composition:

| Stream B | % |
|---|---|
| p-diisopropylbenzene dihydroperoxide | 31.3 |
| p-diisopropylbenzene monohydroperoxide | 2.9 |
| a-hydroxy-a'-hydroperoxydiisopropylbenzene | 2.1 |
| p-diisopropylbenzene | 0.8 |
| Water | 2.5 |
| Benzene | 59.2 |
| Others | 1.2 |

Both streams were dissolved in acetone and combined in a weight ratio of Stream B to Stream A of about 10:1 to provide a feed to the rearranger having the following composition:

| | % |
|---|---|
| p-diisopropylbenzene dihydroperoxide | 16.9 |
| p-diisopropylbenzene monohydroperoxide | 4.4 |
| a-hydroxy-a'-hydroperoxydiisopropylbenzene | 1.4 |
| p-diisopropylbenzene | 0.45 |
| Water | 1.3 |
| Acetone | 44.8 |
| Benzene | 28.8 |
| Others (includes p-acetyl-a-hydroxy-isopropylbenzene) | 2.0 |

Sulfuric acid having a strength of 95 to 97% by weight was employed as the catalyst and was fed at a rate slightly in excess of an amount sufficient to cleave all the hydroperoxide. The rearranger effluent had the following composition:

|  | % |
|---|---|
| hydroquinone | 8.2 |
| p-isopropylphenol | 3.1 |
| p-diisopropylbenzene | 0.4 |
| Water | 2.0 |
| Acetone | 54.8 |
| Benzene | 28.8 |
| Others | 2.7 |

As can be seen from the above, employing the process of the present invention, all of the polyhydroperoxide and the monohydroperoxide are converted into the corresponding polyphenol, i.e. hydroquinone, or monophenol, i.e. p-isopropylphenol. It was found that the hydroquinone produced according to the process of the present invention, i.e. by combining the dihydroperoxide originally separated from the oxidation reaction product with the heavy stream from the recycle stream treatment zone 15 was of a quality comparable to that obtained using only the dihydroperoxide fraction from zone 12 alone. It should also be observed that the rearranger effluent containing no hydroperoxides presented no disposal problems, the p-isopropylphenol being relatively easily handled.

I claim:

1. In a process wherein an aralkyl tertiary polyhydroperoxide is obtained by the oxidation of an aryl tertiary alkane with an oxygen containing gas at elevated temperatures and there are produced, in addition to said aralkyl tertiary polyhydroperoxide, aralkyl tertiary monohydroperoxide, and certain by-products, and wherein an oxidation product fraction containing said polyhydroperoxide is separated from the oxidation reaction product and at least a portion of the resultant recycle stream containing unreacted aryl tertiary alkane, aralkyl tertiary monohydroperoxide, a minor amount of said polyhydroperoxide and said by-products is separated into a first lighter fraction containing primarily said monohydroperoxide and aryl tertiary alkane and a second heavier fraction containing substantially all of said polyhydroperoxide, and at least a portion of said by-products, the remaining portion of said recycle stream being recycled to said oxidation, the improvement comprising; introducing a portion of said second fraction into a rearrangement zone employing an acid catalyst and cleaving at least a portion of said polyhydroperoxide contained therein to the corresponding polyphenol.

2. The process of claim 1 wherein said second fraction is combined with said oxidation product fraction containing said greater portion of said polyhydroperoxide separated from said reaction product prior to introduction into said rearrangement zone.

3. The process of claim 1 wherein said aralkyl tertiary polyhydroperoxide comprises p-diisopropylbenzene dihydroperoxide and said aralkyl tertiary monohydroperoxide comprises p-diisopropylbenzene monohydroperoxide.

4. The process of claim 2 wherein the weight ratio of said oxidation product fraction containing said polyhydroperoxide separated from said reaction product to said second fraction is from about 5 to 1 to about 20 to 1.

5. The process of claim 1 wherein said second fraction is dissolved in a solvent prior to introduction into said rearrangement zone.

6. The process of claim 5 wherein said solvent comprises a ketone which is the same as the ketone obtained from rearrangement of said polyhydroperoxide.

7. A process for treating an oxidation reaction product obtained by oxidizing an aralkyl tertiary alkane with an oxygen containing gas at elevated temperatures to produce the corresponding polyphenol comprising:
  a. separating from said oxidation reaction product an oxidation product fraction containing the aralkyl tertiary polyhydroperoxide produced and recovering a recycle stream containing aryl tertiary alkane, aralkyl tertiary monohydroperoxide, a minor amount of said polyhydroperoxide and other by-products;
  b. introducing a portion of said recycle stream into a separation zone;
  c. recycling the remaining portion of said recycle stream to the oxidation reaction;
  d. separating said portion of said recycle stream into a first lighter fraction containing primarily said monohydroperoxide and aryl tertiary alkane and a second heavier fraction containing substantially all of said polyhydroperoxide, and at least a portion of said by-products;
  e. introducing at least a portion of said second fraction into a rearrangement zone employing an acid catalyst; and
  f. cleaving at least a portion of said polyhydroperoxide contained therein to the corresponding polyphenol.

8. The process of claim 7 wherein said second fraction is combined with oxidation product fraction containing said polyhydroperoxide separated from said reaction product prior to introduction into said rearrangement zone.

9. The process of claim 7 wherein said aralkyl tertiary polyhydroperoxide comprises p-diisopropylbenzene dihydroperoxide and aralkyl tertiary monohydroperoxide comprises p-diisopropylbenzene monohydroperoxide.

10. The process of claim 8 wherein the weight ratio of said oxidation product fraction containing said polyhydroperoxide separated from said reaction product to said second fraction is from about 5 to 1 to about 20 to 1.

11. The process of claim 7 wherein said second fraction is dissolved in a solvent prior to introduction into said rearrangement zone.

12. The process of claim 11 wherein said solvent comprises a ketone which is the same as the ketone obtained from rearrangement of said polyhydroperoxide.

13. A process for producing a polyphenol by treating the heavier portion of a purge stream derived from an oxidation reaction product obtained by oxidizing an aralkyl tertiary alkane with an oxygen containing gas at elevated temperatures to produce an aralkyl tertiary polyhydroperoxide, said heavier portion of said purge stream comprising a fraction of a recycle stream and containing aralkyl tertiary monohydroperoxide, a minor amount of said polyhydroperoxide and oxidation reaction by-products, said by-products including keto aryl tertiary alkanols and aralkyl tertiary dialkanols, comprising introducing said heavier portion of said purge stream into a rearrangement zone employing an acid catalyst and cleaving at least a portion of said polyhydroperoxide contained therein to the corresponding polyphenol.

14. The process of claim 13 wherein said aralkyl tertiary alkane comprises p-diisopropylbenzene, said aralkyl tertiary polyhydroperoxide comprises p-diisopropylbenzene dihydroperoxide said aralkyl tertiary monohydroperoxide comprises p-diisopropylbenzene monohydroperoxide, said keto aryl tertiary alkanol comprises p-acetyl-a-hydroxyisopropylbenzene and said aralkyl tertiary dialkanol comprises p-a-a'-dihydroxyisopropylbenzene.

15. The process of claim 13 wherein said portion of said purge stream is dissolved in a solvent prior to introduction into said rearrangement zone.

16. The process of claim 15 wherein said solvent comprises a ketone which is the same as the ketone obtained from rearrangement of said polyhydroperoxide.

17. The process of claim 13 wherein said oxidation reaction by-products are present in an amount of from about 5 to about 35% by weight.

* * * * *

UNITED STATES PATENT AND TRADEMARK OFFICE
CERTIFICATE OF CORRECTION

PATENT NO. : 3,978,142
DATED : August 31, 1976
INVENTOR(S) : Ward J. Burkholder

It is certified that error appears in the above–identified patent and that said Letters Patent are hereby corrected as shown below:

In Column 1, line 48, delete the word "it", and insert therefor --if--.

In Column 2, line 46, after the word by-products, delete "," and insert therefor --. The first fraction is recycled to the oxidizer while the second fraction--.

In Column 4, line 34, after the word, atmospheric, delete "sub-atmospheric".

In Column 10, line 41, after the word and, insert the word --said--.

Signed and Sealed this sixteenth Day of August 1977

[SEAL]

Attest:

RUTH C. MASON
Attesting Officer

C. MARSHALL DANN
Commissioner of Patents and Trademark